(12) United States Patent
Liu

(10) Patent No.: US 10,646,133 B2
(45) Date of Patent: May 12, 2020

(54) DOMINANT EYE DETERMINING METHOD AND DEVICE

(71) Applicant: Beijing Zhigu Rui Tuo Tech Co., Ltd, Beijing (CN)

(72) Inventor: Hao Liu, Beijing (CN)

(73) Assignee: Beijing Zhigu Rui Tuo Tech Co., Ltd, Beijing (CN)

( * ) Notice: Subject to any disclaimer, the term of this patent is extended or adjusted under 35 U.S.C. 154(b) by 349 days.

(21) Appl. No.: 15/525,040

(22) PCT Filed: Jul. 24, 2015

(86) PCT No.: PCT/CN2015/085024
§ 371 (c)(1),
(2) Date: May 5, 2017

(87) PCT Pub. No.: WO2016/070653
PCT Pub. Date: May 12, 2016

(65) Prior Publication Data
US 2018/0279902 A1    Oct. 4, 2018

(30) Foreign Application Priority Data

Nov. 7, 2014   (CN) .......................... 2014 1 0642561
Nov. 7, 2014   (CN) .......................... 2014 1 0643721
(Continued)

(51) Int. Cl.
*A61B 5/04*   (2006.01)
*A61B 5/0496*   (2006.01)
(Continued)

(52) U.S. Cl.
CPC ............ *A61B 5/0496* (2013.01); *A61B 3/113* (2013.01); *A61B 5/7278* (2013.01); *G06F 3/013* (2013.01)

(58) Field of Classification Search
CPC ..... A61B 5/0496; A61B 5/7278; A61B 3/113; G06F 3/013; A61F 2009/00846
(Continued)

(56) References Cited

U.S. PATENT DOCUMENTS 7,554,549 B2   6/2009   Sagar et al.
8,405,610 B1   3/2013   Cole
(Continued)

FOREIGN PATENT DOCUMENTS

CN   101019760 A   8/2007
CN   102264277 A   11/2011
(Continued)

OTHER PUBLICATIONS

International Search Report for PCT Application No. PCT/CN2015/085024, dated Oct. 28, 2015, 4 pages.
(Continued)

*Primary Examiner* — William R Alexander
*Assistant Examiner* — Henry A Duong
(74) *Attorney, Agent, or Firm* — Amin, Turocy & Watson, LLP

(57) ABSTRACT

This application relates to the field of wearable devices and provides a dominant eye determining method and device. A method comprises: obtaining first sensory information of a first eye of a user; and determining whether the first eye is a dominant eye according to the first sensory information and reference information. The method and device help other devices worn by a user to perform automatic set-up according to a determining result, thereby improving user experience.

53 Claims, 15 Drawing Sheets

Obtain first sensory information of a first eye of a user — S120

Determine whether the first eye is a dominant eye according to the first sensory information and reference information — S140

(30) Foreign Application Priority Data

Nov. 7, 2014 (CN) .......................... 2014 1 0643724
Nov. 7, 2014 (CN) .......................... 2014 1 0643947

(51) Int. Cl.
*G06F 3/01* (2006.01)
*A61B 3/113* (2006.01)
*A61B 5/00* (2006.01)

(58) Field of Classification Search
USPC ....................................................... 351/209
See application file for complete search history.

(56) References Cited

U.S. PATENT DOCUMENTS

| | | | |
|---|---|---|---|
| 8,862,217 | B2 | 10/2014 | Mckinley et al. |
| 9,319,662 | B2 | 4/2016 | Bathiche et al. |
| 2012/0029322 | A1 | 2/2012 | Wartena et al. |
| 2014/0200079 | A1 | 7/2014 | Bathiche et al. |
| 2016/0287069 | A1* | 10/2016 | Haddadi ................ A61B 3/113 |

FOREIGN PATENT DOCUMENTS

| | | |
|---|---|---|
| CN | 102378596 A | 3/2012 |
| CN | 203354540 U | 12/2013 |
| CN | 104133554 A | 11/2014 |
| CN | 104360739 A | 2/2015 |
| CN | 104360740 A | 2/2015 |
| CN | 104367320 A | 2/2015 |
| CN | 104375644 A | 2/2015 |
| JP | 2012100756 A | 5/2012 |

OTHER PUBLICATIONS

Guan Yongqing, et al. "Visual evoked potentials and eye dominance," Journal of Modern Electrophysiology, vol. 5 No. 4 (1998): 154-155.

* cited by examiner

US 10,646,133 B2

DOMINANT EYE DETERMINING METHOD AND DEVICE

RELATED APPLICATION

The present application is a U.S. National Stage filing under 35 U.S.C. § 371 of international patent cooperation treaty (PCT) application No. PCT/CN2015/085024, filed Jul. 24, 2015, and entitled "DOMINANT EYE DETERMINING METHOD AND DEVICE", which claims the benefit of priority to four Chinese Patent Application Nos. 201410642561.1, No. 201410643724.8, No. 201410643721.4 and No. 201410643947.4, which applications were all filed on Nov. 7, 2014, and which applications are hereby incorporated into the present international PCT application by reference herein in their respective entireties.

TECHNICAL FIELD

This application relates to the field of wearable devices, and in particular, to a dominant eye determining method and device.

BACKGROUND

In recent years, with the development of wearable devices, smart wristbands, smart bracelets, smart glasses, and the like gradually enter the life of people, and greatly enrich and facilitate the life of people. Because of a small size, the interaction capability of the wearable device is poor. Therefore, normally, people hope that the wearable device has a good self-identifying capability, thereby reducing set operations of a user.

When people are looking at something, functions of the two eyes are always different. One of the eyes is always in a dominant position to some degree, and becomes a primarily eye responsible for positioning and causing fusion, and this eye is referred to as the dominant eye. The dominant eye is one of common traits of lateral functional dominance of human beings. A determining result of the dominant eye can be used to improve game experience, view experience, and the like of a user. For example, immersive interaction experience of a user is improved by using the dominant eye to perform aiming in a shooting game.

If a wearable device can determine the dominant eye of a user, the dominant eye may be used as input from the wearable device or another device, thereby reducing set operations of the user and improving using experience of the user.

SUMMARY

An example, non-limiting objective of this application is to provide a dominant eye determining method and device.

According to one aspect of at least one example embodiment of this application, a dominant eye determining method is provided, and the method comprises:
  obtaining first sensory information of a first eye of a user; and
  determining whether the first eye is a dominant eye according to the first sensory information and reference information.

According to another aspect of at least one example embodiment of this application, a dominant eye determining device is provided, and the device comprises:
  a first obtaining module, configured to obtain first sensory information of a first eye of a user; and
  a determining module, configured to determine whether the first eye is a dominant eye according to the first sensory information and reference information.

In the dominant eye determining method and device of the example embodiments of this application, first sensory information of a first eye of a user is obtained, and then whether the first eye is a dominant eye is determined according to the first sensory information and reference information, so that a determining method of the dominant eye is provided, which helps a device worn by the user to perform automatic set-up according to a determining result, thereby improving user experience.

DETAILED DESCRIPTION

Example embodiments of this application are further described in detail below with reference to the accompanying drawings and embodiments. The following embodiments are used to describe this application, but are not intended to limit the scope of this application.

A person skilled in the art understands that in the embodiments of this application, sequence numbers of the following steps do not mean execution sequences. The execution sequences of the steps should be determined according to functions and internal logic of the steps, and should not be construed as any limitation on the implementation processes of the embodiments of this application.

Figure 1:
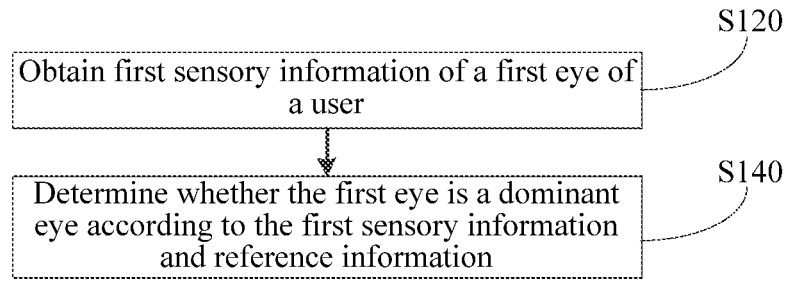
FIG. 1 is a flowchart of a dominant eye determining method in an example embodiment of this application.

FIG. 1 is a flowchart of a dominant eye determining method in an embodiment of this application. The method may be implemented, for example, in a dominant eye determining device. As shown in FIG. 1, the method comprises:

S120: Obtain first sensory information of a first eye of a user.

S140: Determine whether the first eye is a dominant eye according to the first sensory information and reference information.

In the method of an example embodiment of this application, first sensory information of a first eye of a user is obtained, and then whether the first eye is a dominant eye is determined according to the first sensory information and reference information, so that a dominant eye determining method is provided, which helps a wearable device of the user to perform automatic set-up according to a determining result, thereby improving user experience.

Functions of steps S120 and S140 are described in detail below with reference to example embodiments.

S120: Obtain first sensory information of a first eye of a user.

The first eye is the left eye or the right eye of the user.

The first sensory information may be EOG information, EMG information or temperature information of the first eye, EEG information corresponding to the first eye, or the like, and may be obtained by using a corresponding sensor or collecting system. For example, the EOG information of the first eye may be obtained by using at least one EOG sensor, the EMG information of the first eye may be obtained by using at least one EMG sensor, the temperature information of the first eye may be obtained by using at least one temperature sensor, and the EEG information corresponding to the first eye may be obtained by using at least one EEG sensor.

The EMG information of the first eye may be EMG information of a muscle corresponding to the first eye; the temperature information of the first eye may be the temperature of an eyeball of the first eye; and when the first eye is the left eye, the EEG information corresponding to the first eye may be EEG information corresponding to an FP1 area of a brain, and when the first eye is the right eye, the EEG information corresponding to the first eye may be EEG information corresponding to an FP2 area of a brain.

S140: Determine whether the first eye is a dominant eye according to the first sensory information and reference information.

a) The first sensory information may be the EOG information of the first eye, that is, first EOG information. The step S140 is:

S140a: Determine whether the first eye is the dominant eye according to the first EOG information and the reference information.

It is noted that eyeball movement of a person mainly falls in a range of 0 to 60 degree. When an eyeball of the user moves, an electric potential difference is caused to be generated between a retina and a cornea of the eyeball. An EOG sensor may record, by using an electrode, the electric potential difference generated eye movement. When a deflection angle of eye movement falls in a range of 0 to 30 degree, the electric potential difference and the eyeball deflection angle conform to a linear relationship; and when the deflection angle of eye movement falls in a range of 30 to 60 degree, the electric potential difference and the eyeball deflection angle conform to a sinusoidal relationship.

In addition, it is noted that frequency and a deflection angle of eye movement of a dominant eye of a person are higher than those of a non-dominant eye. It is noted that after EOG signals are collected separately at a same position of the dominant eye and non-dominant eye of the user with same sampling frequency within a period, an average amplitude value of an EOG signal of the dominant eye is obviously higher than an average amplitude value of an EOG signal of the non-dominant eye.

Figure 2:
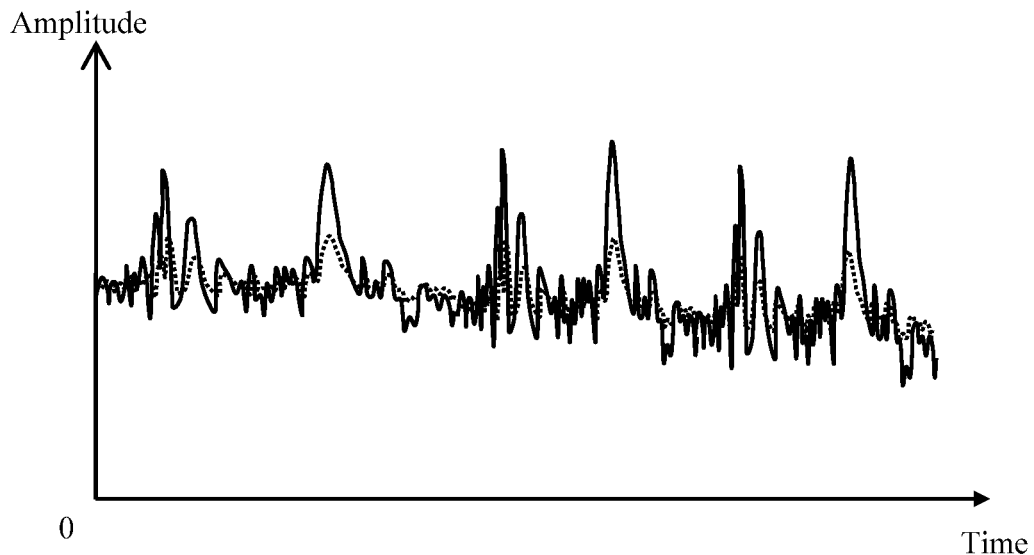
FIG. 2 is a schematic diagram of an example comparison between electro-oculogram (EOG) signals of a dominant eye and a non-dominant eye.

FIG. 2 is a schematic diagram of comparison between EOG signals of a dominant eye and a non-dominant eye of the user. The horizontal axis represents time, the vertical axis represents an amplitude value of an EOG signal, a solid-line curve represents an EOG signal curve of the dominant eye, and a dashed curve represents an EOG signal curve of the non-dominant eye. It can be seen that an amplitude value of the EOG signal of the dominant eye is generally higher than an amplitude value of the EOG signal of the non-dominant eye. Based on the foregoing principle, determining of the dominant eye can be implemented.

An amplitude value of various types of sensory information (comprising EOG information, EEG information, and EMG information) in this application refers to amplitude of a waveform corresponding to corresponding sensory information, and the amplitude value is always a negative value.

In an example embodiment, the reference information is second EOG information of a second eye of the user. The method may further comprise:

S130a: Obtain second EOG information of a second eye of the user as the reference information.

For example, two sets of the EOG sensors may be set, and EOG information of the first eye and the second eye of the user is collected simultaneously. The collected EOG information of the second eye, that is, the second EOG information, is used as the reference information.

Figure 3:
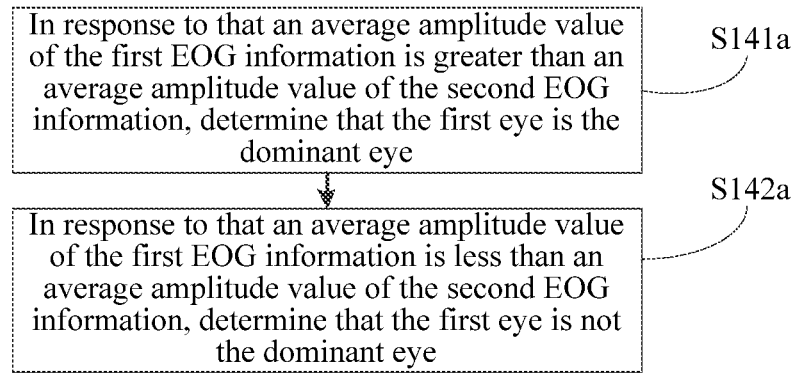
FIG. 3 is detailed flowchart of step S140a in an example embodiment of this application.

In this example embodiment, the step S140a may determine whether the first eye is the dominant eye by comparing an average amplitude value of the first EOG information with an average amplitude value of the second EOG information. The average amplitude value of the first EOG information is an average value of EOG amplitude values corresponding to multiple sampling points in the first EOG information, and similarly, the average amplitude value of the second EOG information is an average value of EOG amplitude values corresponding to multiple sampling points in the second EOG information. By using an average value, a determining error caused by a sampling error of a single sampling point is avoided, thereby improving accuracy of determining. Specifically, as shown in FIG. 3, the step S140a may comprise:

S141a: In response to that an average amplitude value of the first EOG information is greater than an average amplitude value of the second EOG information, determine that the first eye is the dominant eye.

S142a: In response to that an average amplitude value of the first EOG information is less than an average amplitude value of the second EOG information, determine that the first eye is not the dominant eye.

Figure 4:
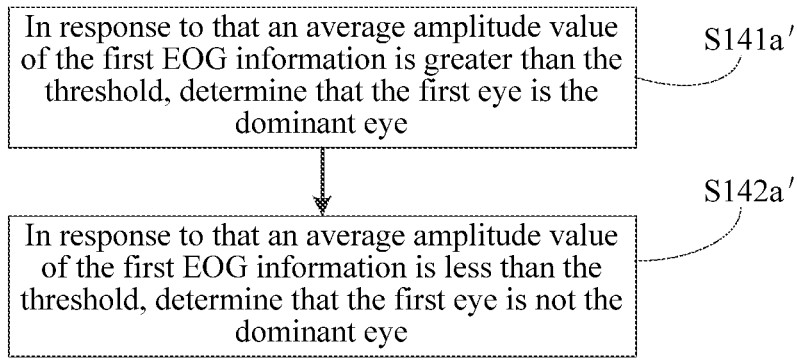
FIG. 4 is detailed flowchart of step S140a in another example embodiment of this application.

In another example embodiment, the reference information may be a threshold determined according to an average amplitude value of left-eye EOG information of the user and an average amplitude value of right-eye EOG information of the user. Specifically, as shown in FIG. 4, the step S140a may comprise:

S141a': In response to that an average amplitude value of the first EOG information is greater than the threshold, determine that the first eye is the dominant eye.

S142a': In response to that an average amplitude value of the first EOG information is less than the threshold, determine that the first eye is not the dominant eye.

For example, the right-eye EOG information and the left-eye EOG information of the user are collected in advance, and are analyzed and processed. Assuming that the average amplitude value of the right-eye EOG information falls in a first range of $(R_{omin}, R_{omax})$, assuming that the average amplitude value of the left-eye EOG information falls in a second range of $(L_{omin}, L_{omax})$, and assuming that the right eye is the dominant eye, then $L_{omax} < R_{omin}$, and the threshold may be determined as $M_o$, and $L_{omax} < M_o < R_{omin}$. That is, the threshold $M_o$ is a numerical value between the first range and the second range.

Therefore, if the average amplitude value of the first EOG information is greater than the threshold $M_o$, the average amplitude value of the first EOG information is considered as falling in the first range, and the first eye is the dominant eye of the user; and if the average amplitude value of the first EOG information is less than the threshold $M_o$, the average amplitude value of the first EOG information is considered as falling in the second range, and the first eye is not the dominant eye of the user.

Generally, an average amplitude value of EOG information of the dominant eye is 5% higher than an average amplitude value of EOG information of the non-dominant eye, and accordingly the threshold $M_o$ may be set properly.

b) The first sensory information may be the temperature information of the first eye, that is, first temperature information. The step S140 is:

S140b: Determine whether the first eye is the dominant eye according to the first temperature information and the reference information.

It is noted that blood-supply of an eyeball comes from an ophthalmic artery. The ophthalmic artery enters the orbit through an optic canal after separating from an internal carotid artery, and is divided into two independent systems: a central retinal vascular system, supplying blood to several inner retinal layers; and a ciliary vascular system, supplying blood to other parts of the eyeball except parts supplied by a central retinal artery. It is noted that because of results of natural evolution, blood vessels of the central retinal vascular system and the ciliary vascular system of the dominant eye are thicker and supply more blood than those of the non-dominant eye. Therefore, it causes that the temperature of the dominant eye is higher than the temperature of the non-dominant eye.

In addition, it is noted that frequency and a deflection angle of eye movement of the dominant eye of a person are obviously higher than those of the non-dominant eye, and the eye movement generates heat, which therefore also causes that the temperature of the dominant eye is higher than the temperature of the non-dominant eye.

Figure 5:
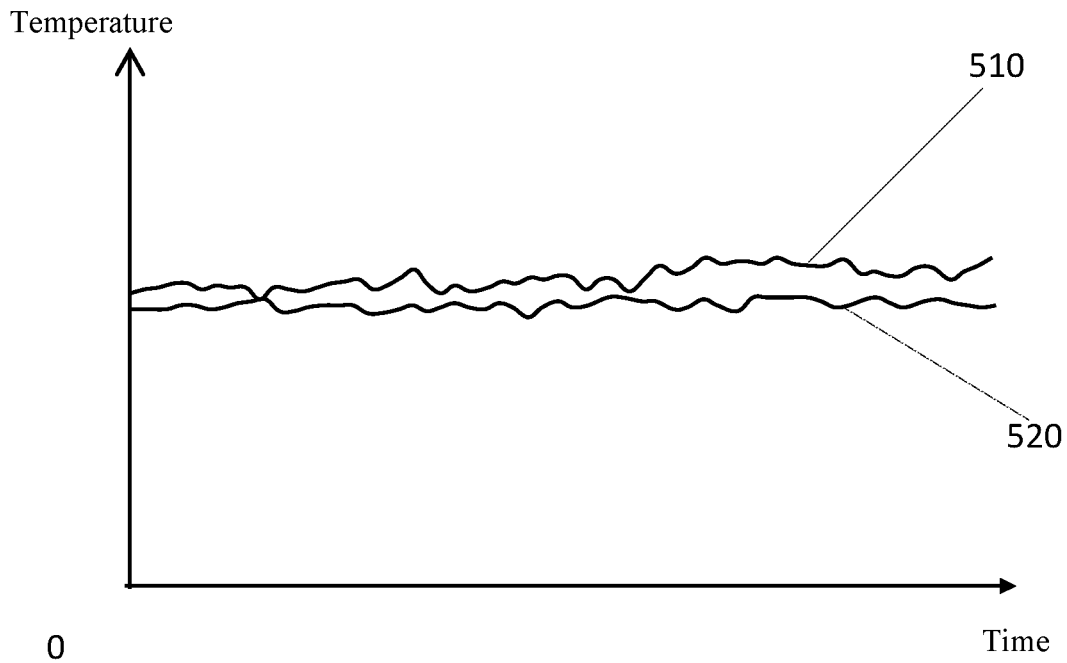
FIG. 5 is a schematic diagram of comparison between temperature information of a dominant eye and a non-dominant eye.

FIG. 5 is a schematic diagram of comparison between temperature information of a dominant eye and a non-dominant eye of the user. The horizontal axis represents time, the vertical axis represents temperature of an eye, a first curve 510 represents a temperature signal curve of the dominant eye, and a second curve 520 represents a temperature signal curve of the non-dominant eye. It can be seen that a temperature value of the dominant eye is generally higher than a temperature value of the non-dominant eye. Based on the foregoing principle, determining of the dominant eye can be implemented.

In an example embodiment, the reference information is temperature information of a second eye of the user. The method may further comprise:

S130b: Obtain second temperature information of a second eye of the user as the reference information.

For example, two sets of temperature sensors may be set, and temperature information corresponding to the first eye and the second eye of the user is collected simultaneously. The temperature information of the second eye, that is, the second temperature information, is used as the reference information.

Figure 6:
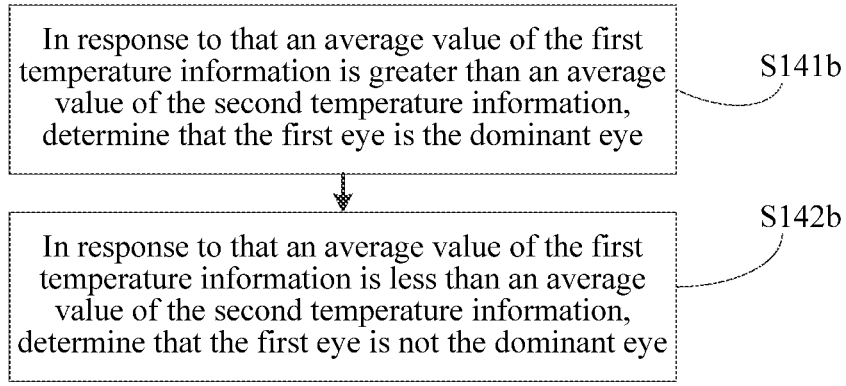
FIG. 6 is detailed flowchart of step S140b in an example embodiment of this application.

In this example embodiment, the step S140b may determine whether the first eye is the dominant eye by comparing an average value of the first temperature information with an average value of the second temperature information. The average value of the first temperature information is an average value of temperature values corresponding to multiple sampling points in the first temperature information, and similarly, the average value of the second temperature information is an average value of temperature values corresponding to multiple sampling points in the second temperature information. By using an average value, a determining error caused by a sampling error of a single sampling point is avoided, thereby improving accuracy of determining. Specifically, referring to FIG. 6, the step S140b may comprise:

S141b: In response to that an average value of the first temperature information is greater than an average value of the second temperature information, determine that the first eye is the dominant eye.

S142b: In response to that an average value of the first temperature information is less than an average value of the second temperature information, determine that the first eye is not the dominant eye.

Figure 7:
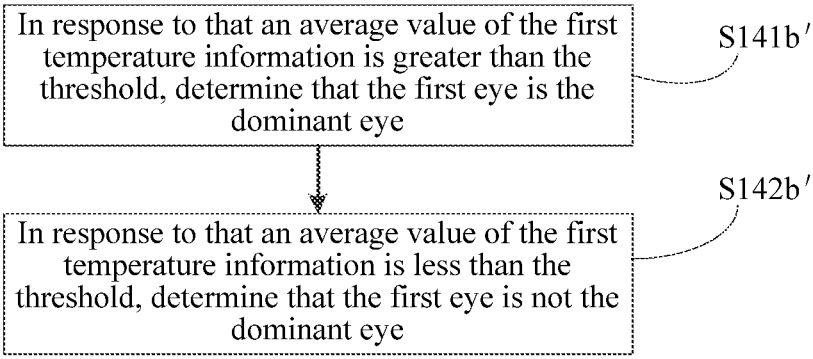
FIG. 7 is detailed flowchart of step S140b in another example embodiment of this application.

In another example embodiment, the reference information may be a threshold determined according to right-eye temperature information and left-eye temperature information of the user. Specifically, referring to FIG. 7, the step S140b may comprise:

S141b': In response to that an average value of the first temperature information is greater than the threshold, determine that the first eye is the dominant eye.

S142b': In response to that an average value of the first temperature information is less than the threshold, determine that the first eye is not the dominant eye.

For example, the left-eye temperature information and the right-eye temperature information of the user are collected in advance, and are analyzed and processed. Assuming that the average value of the left-eye temperature information falls in a first range of ($L_{tmin}$, $L_{tmax}$), assuming that the average value of the right-eye temperature information falls in a second range of ($R_{tmin}$, $R_{tmax}$), and assuming that the right eye is the dominant eye, then $L_{tmax}<R_{tmin}$, and the threshold may be determined as $M_t$, and $L_{tmax}<M_t<R_{tmin}$. That is, the threshold $M_t$ is a numerical value between the first range and the second range.

Therefore, if the average value of the first temperature information is greater than the threshold $M_t$, the average value of the first temperature information is considered as falling in the second range, and the first eye is the dominant eye of the user; and if the average value of the first temperature information is less than the threshold $M_t$, the average value of the first temperature information is considered as falling in the first range, and the first eye is not the dominant eye of the user.

Generally, the temperature of the dominant eye of the user is 0.1 to 1.2□ higher than the temperature of the non-dominant eye of the user, and the threshold $M_t$ may be set properly according to the temperature difference.

c) The first sensory information may be the EMG information of the first eye, that is, first EMG information. The step S140 is:

S140c: Determine whether the first eye is the dominant eye according to the first EMG information and the reference information.

As described before, it is noted that frequency and a deflection angle of eye movement of a dominant eye of a person are higher than those of a non-dominant eye. In other words, contraction frequency and amplitude of a muscle that controls the dominant eye are higher than contraction frequency and amplitude of a muscle that controls the non-dominant eye.

It is noted that when the muscle contracts at different loads, an amplitude value of EMG information is in direct proportional to the muscle force, that is, when the tension force generated by the muscle is large, the amplitude value of the EMG information is large. Further, when the muscle contracts with strength less than 40% maximum isometric muscle strength (MVC), a relationship between the muscle force and an EMG amplitude value is linear; and when the muscle contracts with strength greater than 60% MVC, a relationship between the muscle force and an EMG amplitude value is also linear, but in this case, a straight slope is larger. When the muscle force falls in 40% to 60% MVC, a relationship between the muscle force and an amplitude value of EMG information is no longer linear, but is still proportional.

Figure 8:
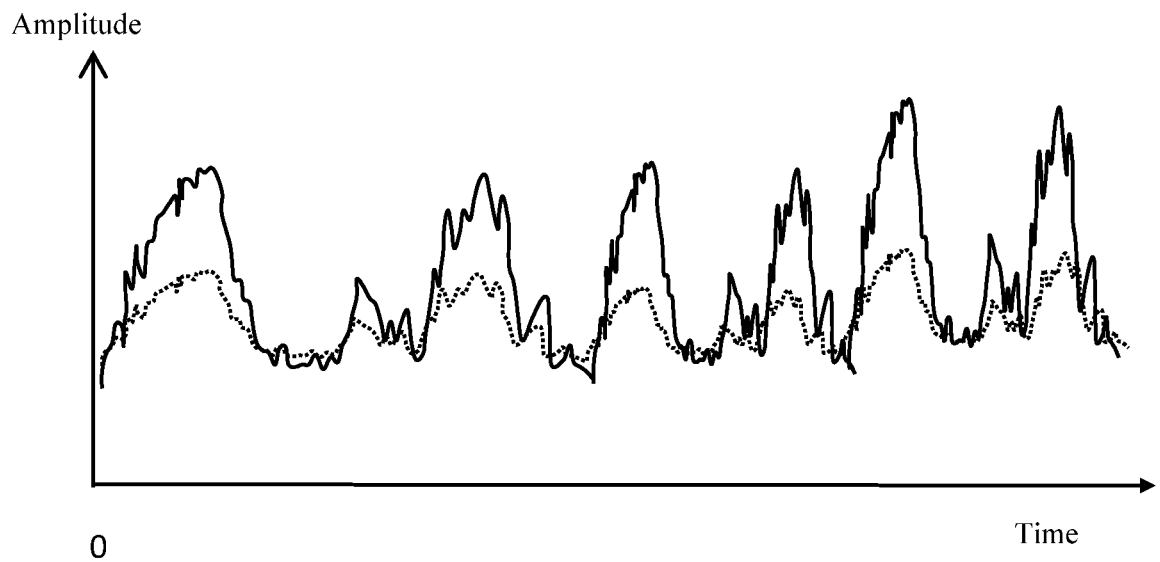
FIG. 8 is a schematic diagram of comparison between electromyogram (EMG) signals of a dominant eye and a non-dominant eye.

FIG. 8 is a schematic diagram of comparison between EMG information obtained through detecting a muscle that controls a dominant eye and a muscle that controls a non-dominant eye within a period. The horizontal axis represents time, the vertical axis represents an amplitude value of an EMG signal, a solid-line curve represents an EMG signal curve of the dominant eye, and a dashed curve represents an EMG signal curve of the non-dominant eye. It can be seen that an amplitude value of the EMG signal of the dominant eye is generally higher than an amplitude value of the EMG signal of the non-dominant eye. Based on the foregoing principle, determining of the dominant eye can be implemented.

In an example embodiment, the reference information is second EMG information of a second eye of the user. The method may further comprise:

S130c: Obtain second EMG information of a second eye of the user as the reference information.

For example, two sets of EMG sensors may be set, and EMG information corresponding to the first eye and the second eye of the user is collected simultaneously. The EMG information of the second eye, that is, the second EMG information, is used as the reference information.

Each eye has six muscles controlling movement of the eyeball. The six muscles are the superior rectus, inferior rectus, medial rectus, lateral rectus, superior oblique, and inferior oblique separately. The six muscles are controlled by the oculomotor nerve, trochlear nerve, and abducent nerve. The medial rectus and lateral rectus mainly control the eyeball to move inward or outward; when the superior rectus and inferior rectus contract, the eyeball moves upward or downward, and the superior rectus and inferior rectus also enable the eyeball to move inward; the superior oblique mainly controls the eyeball to rotate inward, and also enables the eyeball to move downward and outward; and the inferior oblique mainly controls the eyeball to move outward, and also enables the eyeball to move upward and outward. The EMG information may be obtained by detecting all or some of the six muscles.

Figure 9:
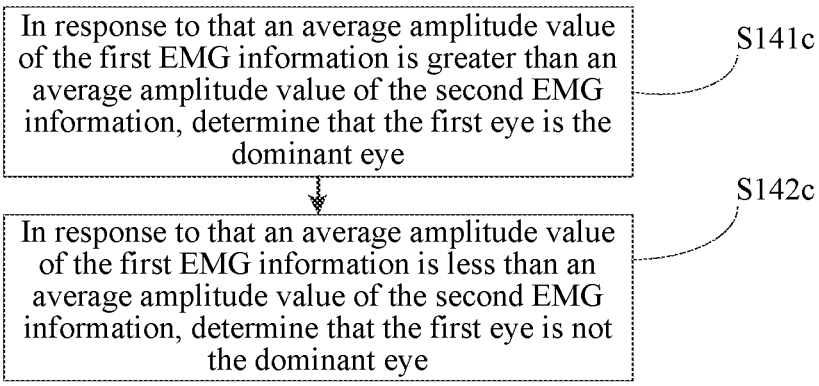
FIG. 9 is detailed flowchart of step S140c in an example embodiment of this application.

In this example embodiment, the step S140c may determine whether the first eye is the dominant eye by comparing an average amplitude value of the first EMG information with an average amplitude value of the second EMG information. The average amplitude value of the first EMG information is an average value of EMG amplitude values corresponding to multiple sampling points in the first EMG information, and similarly, the average amplitude value of the second EMG information is an average value of EMG amplitude values corresponding to multiple sampling points in the second EMG information. By using an average value, a determining error caused by a sampling error of a single sampling point is avoided, thereby improving accuracy of determining. Specifically, referring to FIG. 9, the step S140c may comprise:

S141c: In response to that an average amplitude value of the first EMG information is greater than an average amplitude value of the second EMG information, determine that the first eye is the dominant eye.

S142c: In response to that an average amplitude value of the first EMG information is less than an average amplitude value of the second EMG information, determine that the first eye is not the dominant eye.

Figure 10:
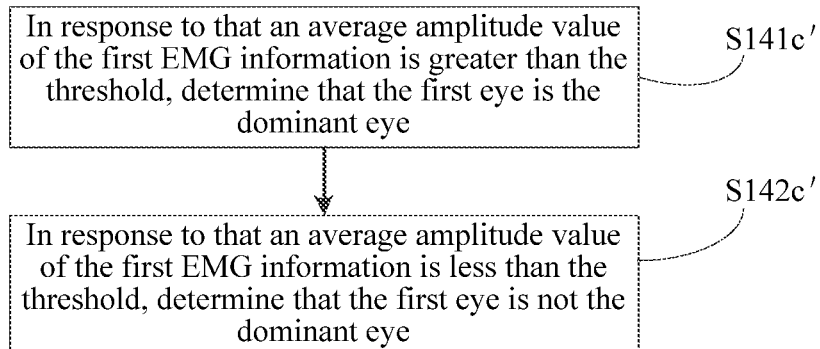
FIG. 10 is detailed flowchart of step S140c in another example embodiment of this application.

In another example embodiment, the reference information may be a threshold determined according to an average amplitude value of right-eye EMG information of the user and an average amplitude value of left-eye EMG information of the user. Specifically, referring to FIG. 10, the step S140c may comprise:

S141c': In response to that an average amplitude value of the first EMG information is greater than the threshold, determine that the first eye is the dominant eye.

S142c': In response to that an average amplitude value of the first EMG information is less than the threshold, determine that the first eye is not the dominant eye.

For example, the right-eye EMG information and the left-eye EMG information of the user are collected in advance, and are analyzed and processed. Assuming that the average amplitude value of the right-eye EMG information falls in a first range of ($R_{mmin}$, $R_{mmax}$), assuming that the average amplitude value of the left-eye EMG information falls in a second range of ($L_{mmin}$, $L_{mmax}$), and assuming that the right eye is the dominant eye, then $L_{mmax} < R_{mmin}$, and the threshold may be determined as $M_m$, and $L_{mmax} < M_m < R_{mmin}$. That is, the threshold $M_m$ is a numerical value between the first range and the second range.

Therefore, if the average amplitude value of the first EMG information is greater than the threshold $M_m$, the average amplitude value of the first EMG information is considered as falling in the first range, and the first eye is the dominant eye of the user; and if the average amplitude value of the first EMG information is less than the threshold $M_m$, the average amplitude value of the first EMG information is considered as falling in the second range, and the first eye is not the dominant eye of the user.

Generally, an average amplitude value of EMG information of the dominant eye is 5% higher than an average amplitude value of EMG information of the non-dominant eye, and accordingly the threshold $M_m$ may be set properly.

d) The first sensory information may be the EEG information corresponding to the first eye, that is, first EEG information.

The step S140 is:

S140d: Determine whether the first eye is the dominant eye according to the first EEG information and the reference information.

As described before, when the eyeball of the user moves, an electric potential difference is caused to be generated between a retina and a cornea of the eyeball. It is noted that the electric potential difference would also be reflected in EEG signals, for example, reflected in EEG signals corresponding to FP1 and FP2 areas in a brain.

Figure 11:
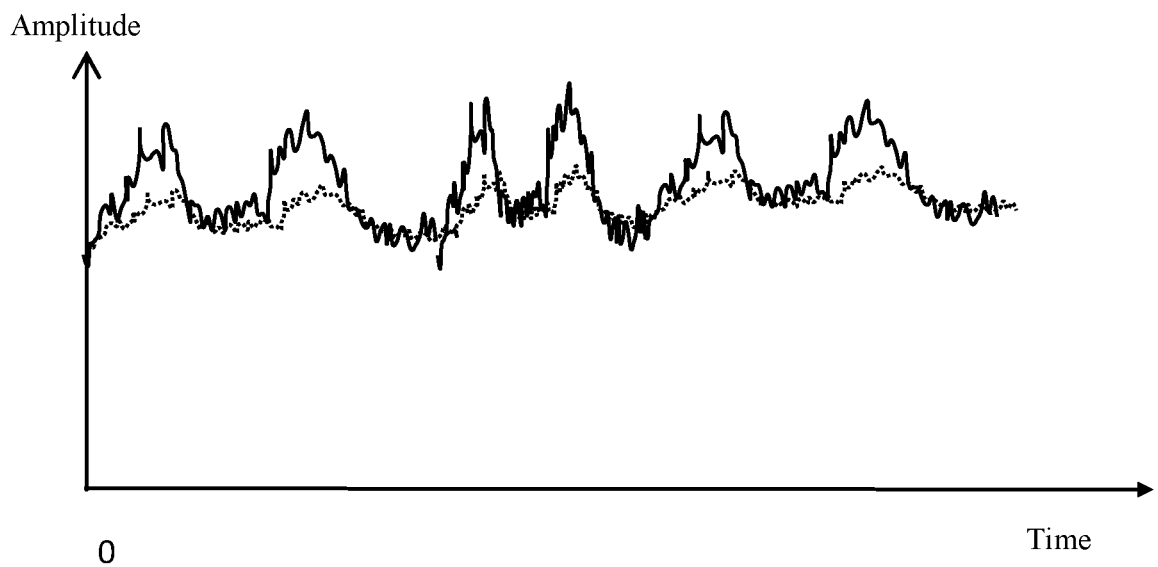
FIG. 11 is a schematic diagram of comparison between electroencephalogram (EEG) signals of a dominant eye and a non-dominant eye.

FIG. 11 is a schematic diagram of comparison between an EEG signal corresponding to the left eye of the user and an EEG signal corresponding to the right eye of the user. The EEG signal corresponding to the left eye is collected at an FP1 position, and the EEG signal corresponding to the right eye is collected at an FP2 position. The horizontal axis represents time, the vertical axis represents an amplitude value of an EEG signal, a solid-line curve represents an EEG signal curve of a dominant eye, and a dashed curve represents an EEG signal curve of a non-dominant eye. It can be seen that an amplitude value of the EEG signal of the dominant eye is generally higher than an amplitude value of the EEG signal of the non-dominant eye. Based on the foregoing principle, determining of the dominant eye can be implemented.

In an example embodiment, the reference information is second EEG information corresponding to a second eye of the user. The method may further comprise:

S130d: Obtain second EEG information corresponding to a second eye of the user as the reference information.

For example, two sets of EEG sensors may be set, and EEG information corresponding to the first eye and the second eye is collected simultaneously at the FP1 area and FP2 area of the brain. The EEG information corresponding to the second eye, that is, the second EEG information, is used as the reference information.

Figure 12:
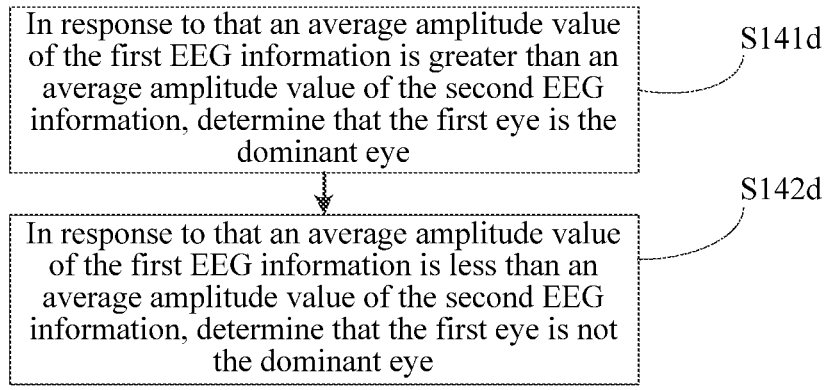
FIG. 12 is detailed flowchart of step S140d in an example embodiment of this application.

In this example embodiment, the step S140d may determine whether the first eye is the dominant eye by comparing an average amplitude value of the first EEG information with an average amplitude value of the second EEG information. The average amplitude value of the first EEG information is an average value of EEG amplitude values corresponding to multiple sampling points in the first EEG information, and similarly, the average amplitude value of the second EEG information is an average value of EEG amplitude values corresponding to multiple sampling points in the second EEG information. By using an average value, a determining error caused by a sampling error of a single sampling point is avoided, thereby improving accuracy of determining. Specifically, referring to FIG. 12, the step S140d may comprise:

S141d: In response to that an average amplitude value of the first EEG information is greater than an average amplitude value of the second EEG information, determine that the first eye is the dominant eye.

S142d: In response to that an average amplitude value of the first EEG information is less than an average amplitude value of the second EEG information, determine that the first eye is not the dominant eye.

Figure 13:
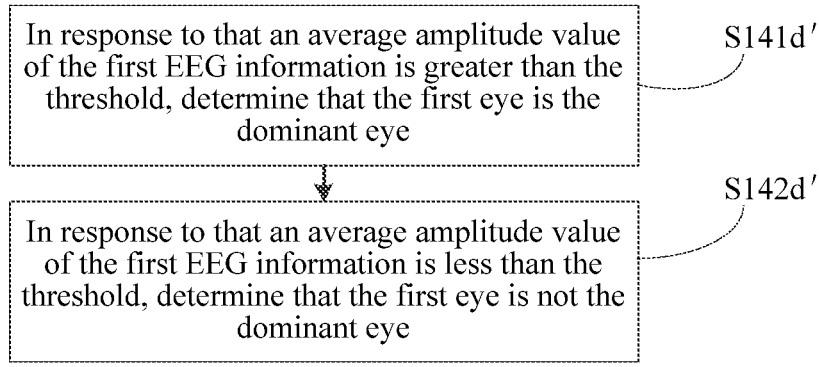
FIG. 13 is detailed flowchart of step S140d in another example embodiment of this application.

In another example embodiment, the reference information may be a threshold determined according to an average amplitude value of left-eye EEG information of the user and an average amplitude value of right-eye EEG information of the user. Specifically, referring to FIG. 13, the step S140d may comprise:

S141d': In response to that an average amplitude value of the first EEG information is greater than the threshold, determine that the first eye is the dominant eye.

S142d': In response to that an average amplitude value of the first EEG information is less than the threshold, determine that the first eye is not the dominant eye.

For example, the left-eye EEG information and the right-eye EEG information of the user are collected in advance, and are analyzed and processed. Assuming that the average amplitude value of the right-eye EEG information falls in a first range of ($R_{emin}$, $R_{emax}$), assuming that the average amplitude value of the left-eye EEG information falls in a second range of ($L_{emin}$, $L_{emax}$), and assuming that the right eye is the dominant eye, then $L_{emax} < R_{emax}$, and the threshold may be determined as $M_e$, and $L_{emax} < M_e < R_{emin}$. That is, the threshold $M_e$ is a numerical value between the first range and the second range.

Therefore, if the average amplitude value of the first EEG information is greater than the threshold $M_e$, the average amplitude value of the first EEG information is considered as falling in the first range, and the first eye is the dominant eye; and if the average amplitude value of the first EEG information is less than the threshold $M_e$, the average amplitude value of the first EEG information is considered as falling in the second range, and the first eye is not the dominant eye.

Generally, an average amplitude value of EEG information of the dominant eye is 5% higher than an average amplitude value of EEG information of the non-dominant eye, and accordingly the threshold $M_e$ may be set properly.

Figure 14:
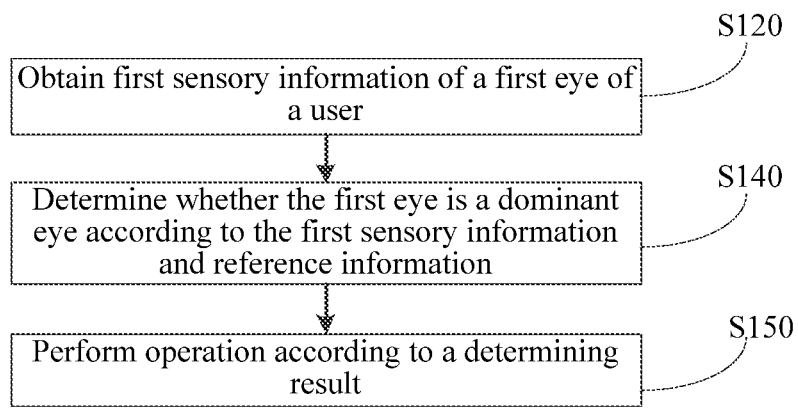
FIG. 14 is a flowchart of a dominant eye determining method in an example embodiment of this application.

Referring to FIG. 14, in an example embodiment, the method may further comprise:

S150: Perform operation according to a determining result.

For example, that the first eye is the dominant eye is displayed according to the determining result. If the user is playing a shooting game, the user may be prompted to use the first eye to perform aiming, so as to improve immersive interaction experience of the user; or, if the user is viewing a 3D film, automatic stereo 3D display at different viewing angles may be performed on the dominant eye and non-dominant eye of the user, to improve visual experience of the user.

Figure 15:
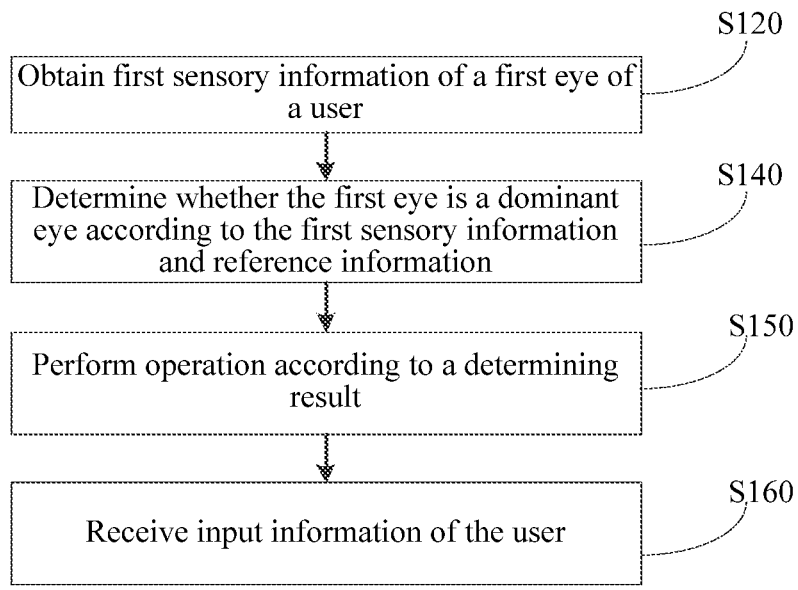
FIG. 15 is a flowchart of a dominant eye determining method in another example embodiment of this application.

Referring to FIG. 15, in an example embodiment, the method may further comprise:

S160: Receive input information of the user.

The user may perform input in a manner of such as voice, key pressing, or gesture.

Figure 16:
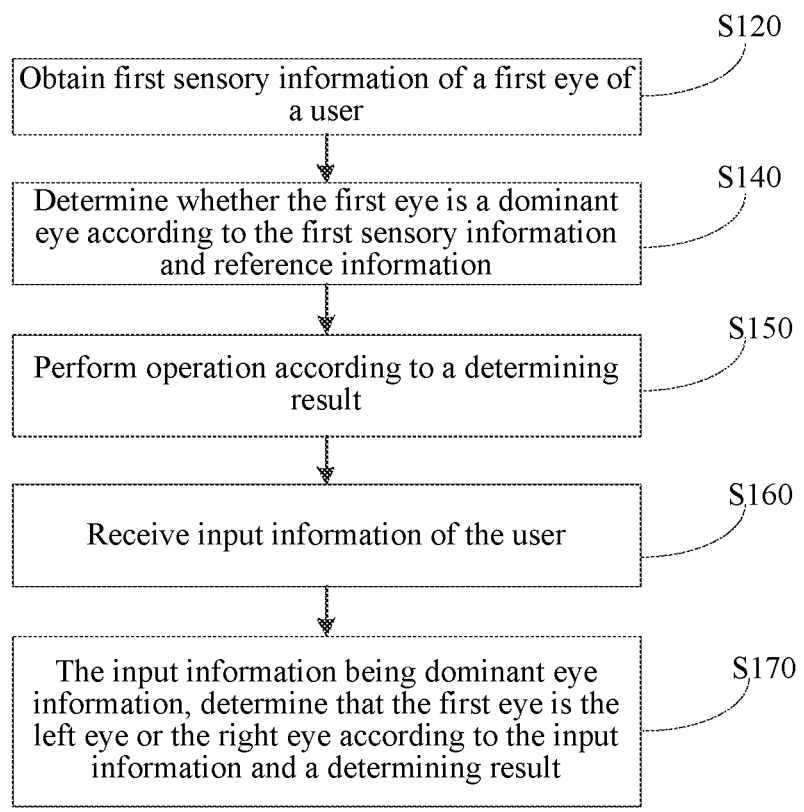
FIG. 16 is a flowchart of a dominant eye determining method in another example embodiment of this application.

Referring to FIG. 16, in an example embodiment, the input information is dominant eye information, that is, information that which eye is the dominant eye, and the method may further comprise:

S170: The input information being dominant eye information, determine that the first eye is the left eye or the right eye according to the input information and a determining result.

For example, the input information shows that the right eye of the user is the dominant eye, and the determining result shows that the first eye is the dominant eye, and then it may be determined that the first eye is the right eye.

After it is determined that the first eye is the left eye or the right eye, related settings of the left eye and right eye may be performed further, for example, a glass lens degree corresponding to the right eye is automatically adjusted to match with a myopic degree of the right eye of the user.

Figure 17:
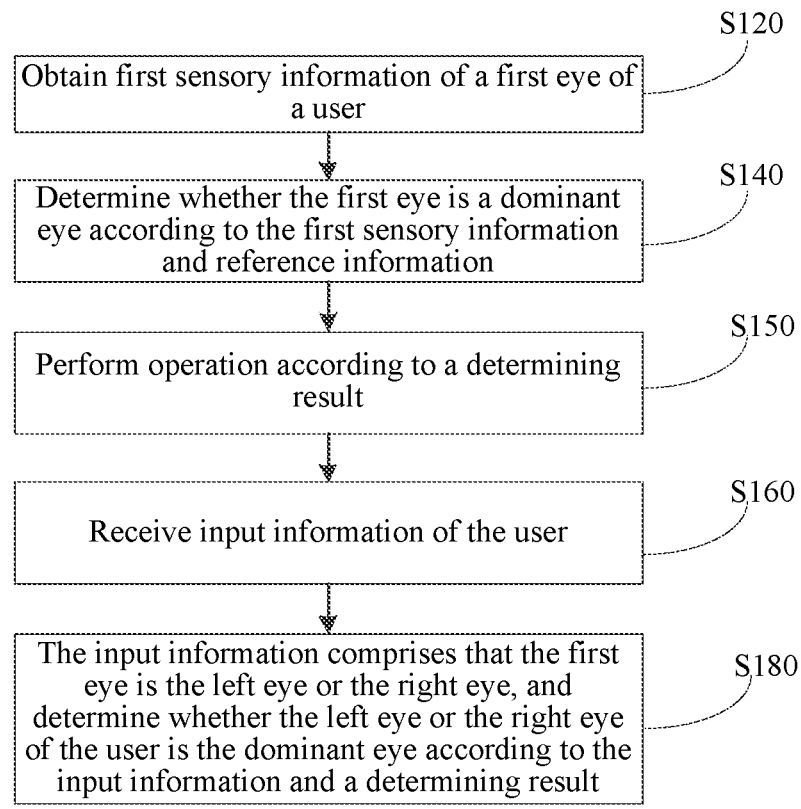
FIG. 17 is a flowchart of a dominant eye determining method in another example embodiment of this application.

Referring to FIG. 17, in an example embodiment, the method may further comprise:

S180: The input information comprises that the first eye is the left eye or the right eye, and determine whether the left eye or the right eye of the user is the dominant eye according to the input information and a determining result.

For example, the input information shows that the first eye is the left eye, and the determining result shows that the first eye is the dominant eye, then it may be determined that the left eye of the user is the dominant eye, and this information may be recorded to be called by another application.

In addition, the embodiments of this application further provide a computer readable medium, which comprises computer readable instructions that perform the following operations when the instructions are executed: perform steps S120 and S140 of the method in the example embodiment shown in FIG. 1.

In conclusion, in the method in the embodiments of this application, whether a first eye is a dominant eye of a user may be determined according to first sensory information of the first eye of the user and reference information, and corresponding operations may be performed according to a determining result, thereby improving user experience.

Figure 18:
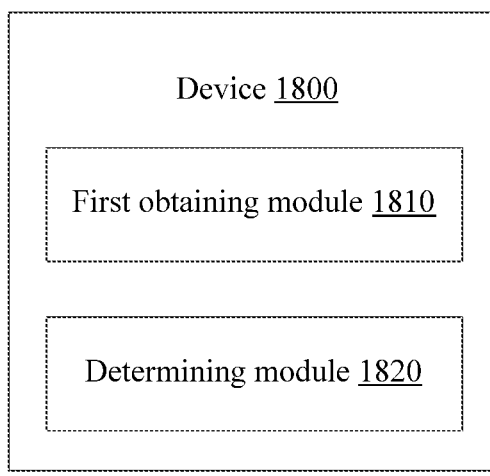
FIG. 18 is a schematic structural module diagram of a dominant eye determining device in an embodiment of this application.

FIG. 18 is a schematic structural module diagram of a dominant eye determining device in an embodiment of this application. The dominant eye determining device may serve as a functional module to be disposed in a wearable device such as a smart helmet, smart glasses, or a smart wig, and may also serve as an independent wearable device to be used by a user. As shown in FIG. 18, the device 1800 may comprise:

a first obtaining module 1810, configured to obtain first sensory information of a first eye of a user; and a determining module 1820, configured to determine whether the first eye is a dominant eye according to the first sensory information and reference information.

In the device of this embodiment of this application, first sensory information of a first eye of a user is obtained, and then whether the first eye is a dominant eye is determined according to the first sensory information and reference information, so that a dominant eye determining device is provided, which helps a wearable device of the user to perform automatic set-up according to a determining result, thereby improving user experience.

Functions of the first obtaining module 1810 and the determining module 1820 are described in detail below with reference to example embodiments.

The first obtaining module 1810 is configured to obtain first sensory information of a first eye of a user.

The first eye is the left eye or the right eye of the user.

The first sensory information may be EOG information, EMG information or temperature information of the first eye, EEG information corresponding to the first eye, or the like, and may be obtained by using a corresponding sensor or collecting system. For example, the EOG information of the first eye may be obtained by using at least one EOG sensor, the EMG information of the first eye may be obtained by using at least one EMG sensor, the temperature information of the first eye may be obtained by using at least one temperature sensor, and all the EEG information corresponding to the first eye may be obtained by using a BP system.

The EMG information of the first eye may be EMG information of a muscle corresponding to the first eye; the temperature information of the first eye may be the temperature of an eyeball of the first eye; and when the first eye is the left eye, the EEG information corresponding to the first eye may be EEG information corresponding to an FP1 area of a brain, and when the first eye is the right eye, the EEG information corresponding to the first eye may be EEG information corresponding to an FP2 area of a brain.

The determining module 1820 is configured to determine whether the first eye is the dominant eye according to the first sensory information and the reference information.

a) The first sensory information may be the EOG information of the first eye, that is, first EOG information. The determining module 1820 is configured to determine whether the first eye is the dominant eye according to the first EOG information and the reference information.

Figure 19:
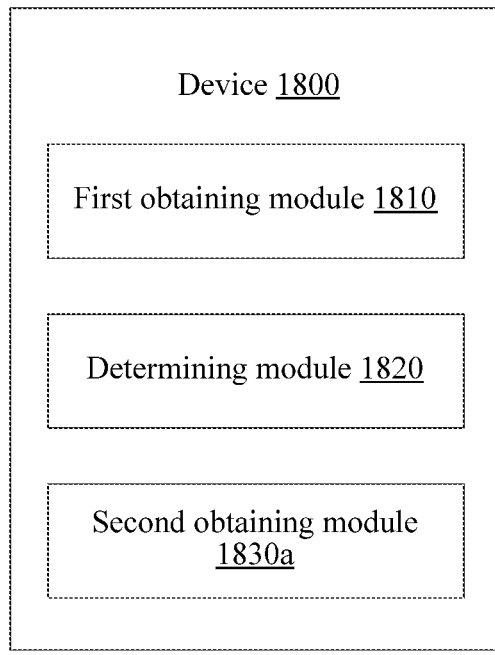
FIG. 19 is a schematic structural module diagram of a dominant eye determining device in an example embodiment of this application.

In an example embodiment, the reference information is second EOG information of a second eye of the user. Referring to FIG. 19, the device 1800 further comprises:

a second obtaining module 1830a, configured to obtain second EOG information of a second eye of the user as the reference information.

Correspondingly, the determining module 1820 is configured to: in response to that an average amplitude value of the first EOG information is greater than an average amplitude value of the second EOG information, determine that the first eye is the dominant eye; and in response to that an average amplitude value of the first EOG information is less than an average amplitude value of the second EOG information, determine that the first eye is not the dominant eye.

Figure 20:
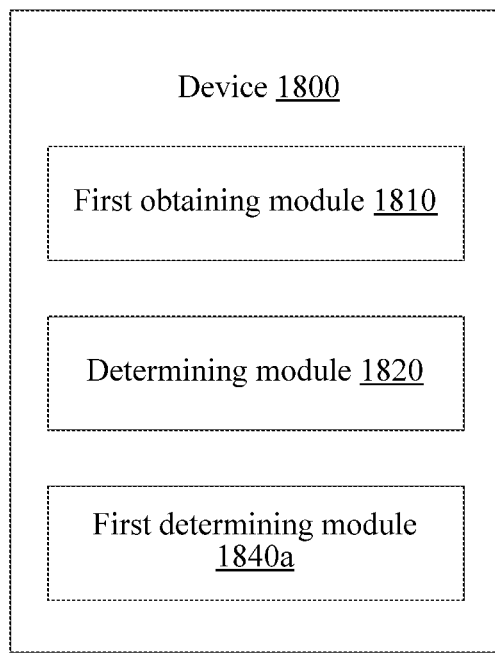
FIG. 20 is a schematic structural module diagram of a dominant eye determining device in another example embodiment of this application.

In another example embodiment, the reference information is a threshold determined according to an average amplitude value of left-eye EOG information of the user and an average amplitude value of right-eye EOG information of the user. Specifically, referring to FIG. 20, the device 1800 further comprises:

a first determining module 1840a, configured to determine a threshold as the reference information according to an average amplitude value of left-eye EOG information of the user and an average amplitude value of right-eye EOG information of the user.

Correspondingly, the determining module 1820 is configured to: in response to that an average amplitude value of the first EOG information is greater than the threshold, determine that the first eye is the dominant eye; and in response to that an average amplitude value of the first EOG information is less than the threshold, determine that the first eye is not the dominant eye.

For example, the first determining module 1840a may collect in advance the right-eye EOG information and the left-eye EOG information of the user, and perform analyzing and processing. Assuming that the average amplitude value of the right-eye EOG information falls in a first range of $(R_{omin}, R_{omax})$, assuming that the average amplitude value of the left-eye EOG information falls in a second range of $(L_{omin}, L_{omax})$, and assuming that the right eye is the dominant eye, then $L_{omax}<R_{omin}$, and the threshold may be determined as $M_o$, and $L_{omax}<M_o<R_{omin}$. That is, the threshold $M_o$ is a numerical value between the first range and the second range.

Therefore, if the average amplitude value of the first EOG information is greater than the threshold $M_o$, the average amplitude value of the first EOG information is considered as falling in the first range, and the first eye is the dominant eye of the user; and if the average amplitude value of the first EOG information is less than the threshold $M_o$, the average amplitude value of the first EOG information is considered as falling in the second range, and the first eye is not the dominant eye of the user.

b) The first sensory information may be the temperature information of the first eye, that is, first temperature information. The determining module 1820 is configured to determine whether the first eye is the dominant eye according to the first temperature information and the reference information.

Figure 21:
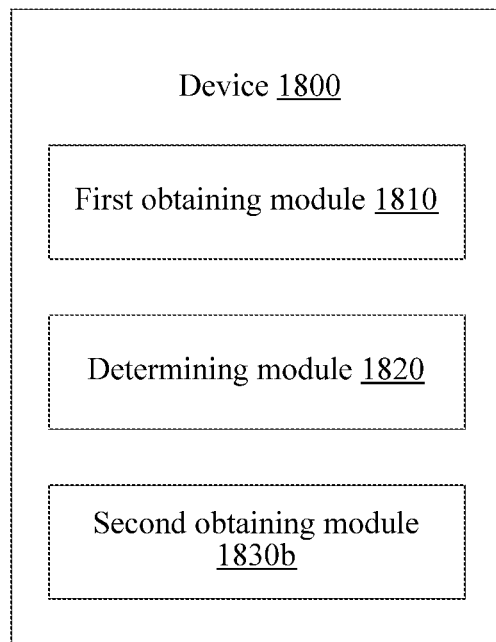
FIG. 21 is a schematic structural module diagram of a dominant eye determining device in another example embodiment of this application.

In an example embodiment, the reference information is second temperature information of a second eye of the user. Referring to FIG. 21, the device 1800 further comprises:

a second obtaining module 1830b, configured to obtain second temperature information of a second eye of the user as the reference information.

Correspondingly, the determining module 1820 is configured to: in response to that an average value of the first temperature information is greater than an average value of the second temperature information, determine that the first eye is the dominant eye; and in response to that an average value of the first temperature information is less than an average value of the second temperature information, determine that the first eye is not the dominant eye.

Figure 22:
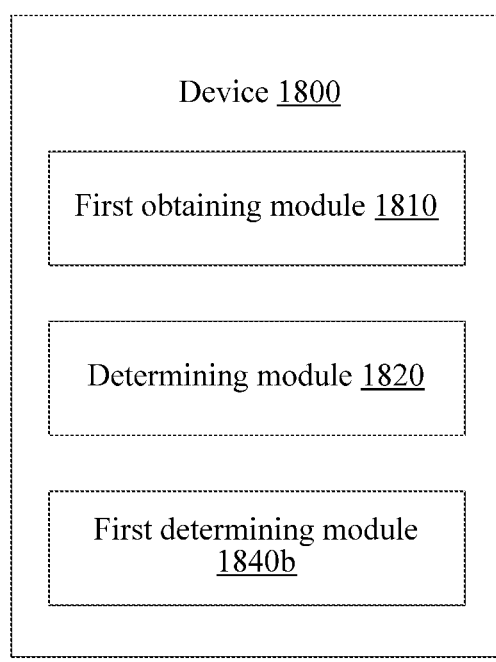
FIG. 22 is a schematic structural module diagram of a dominant eye determining device in another example embodiment of this application.

In another example embodiment, the reference information is a threshold determined according to an average value of left-eye temperature information of the user and an average value of right-eye temperature information of the user. Referring to FIG. 22, the device 1800 further comprises:

a first determining module 1840b, configured to determine a threshold as the reference information according to an average value of left-eye temperature information of the user and an average value of right-eye temperature information of the user.

Correspondingly, the determining module 1820 is configured to: in response to that an average value of the first temperature information is greater than the threshold, determine that the first eye is the dominant eye; and in response to that an average value of the first temperature information is less than the threshold, determine that the first eye is not the dominant eye.

For example, the first determining module 1840b may collect in advance the left-eye temperature information and the right-eye temperature information of the user, and perform analyzing and processing. Assuming that the average value of the left-eye temperature information falls in a first range of $(L_{tmin}, L_{tmax})$, assuming that the average value of the right-eye temperature information falls in a second range of $(R_{tmin}, R_{tmax})$, and assuming that the right eye is the dominant eye, then $L_{tmax}<R_{tmin}$, and the threshold may be determined as $M_t$, and $L_{tmax}<M_t<R_{tmin}$. That is, the threshold $M_t$ is a numerical value between the first range and the second range.

Therefore, if the average value of the first temperature information is greater than the threshold $M_t$, the average value of the first temperature information is considered as falling in the second range, and the first eye is the dominant eye of the user; and if the average value of the first temperature information is less than the threshold $M_t$, the average value of the first temperature information is considered as falling in the first range, and the first eye is not the dominant eye of the user.

c) The first sensory information may also be the EMG information of the first eye, that is, first EMG information. The determining module 1820 is configured to determine whether the first eye is the dominant eye according to the first EMG information and the reference information.

Figure 23:
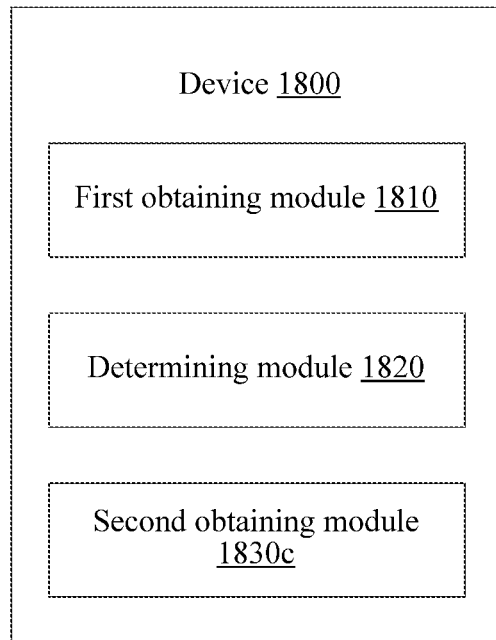
FIG. 23 is a schematic structural module diagram of a dominant eye determining device in another example embodiment of this application.

In an example embodiment, the reference information is second EMG information of a second eye of the user. Referring to FIG. 23, the device 1800 may further comprise:

a second obtaining module 1830c, configured to obtain second EMG information of a second eye of the user as the reference information.

Correspondingly, the determining module 1820 is configured to: in response to that an average amplitude value of the first EMG information is greater than an average amplitude value of the second EMG information, determine that the first eye is the dominant eye; and in response to that an average amplitude value of the first EMG information is less than an average amplitude value of the second EMG information, determine that the first eye is not the dominant eye.

Figure 24:
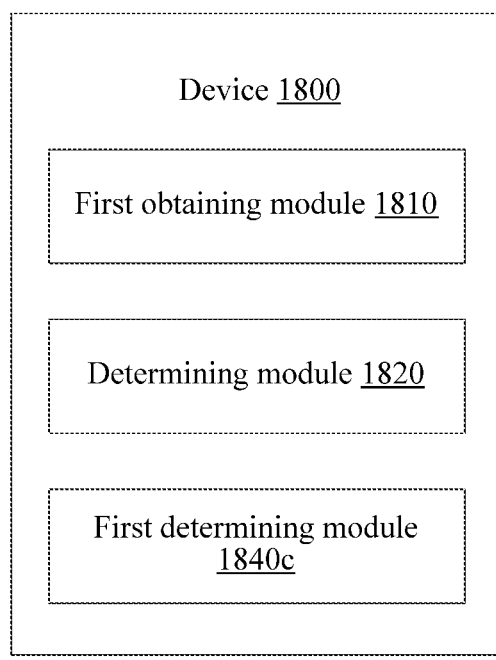
FIG. 24 is a schematic structural module diagram of a dominant eye determining device in another example embodiment of this application.

In another example embodiment, the reference information is a threshold determined according to an average amplitude value of left-eye EMG information of the user and an average amplitude value of right-eye EMG information of the user. Referring to FIG. 24, the device 1800 may further comprise:

a first determining module 1840c, configured to determine a threshold as the reference information according to an average amplitude value of left-eye EMG information of the user and an average amplitude value of right-eye EMG information of the user.

Correspondingly, the determining module 1820 is configured to: in response to that an average amplitude value of the first EMG information is greater than the threshold, determine that the first eye is the dominant eye; and in response to that an average amplitude value of the first EMG information is less than the threshold, determine that the first eye is not the dominant eye.

For example, the first determining module 1840c may collect in advance the right-eye EMG information and the left-eye EMG information of the user, and perform analyzing and processing. Assuming that the average amplitude value of the right-eye EMG information falls in a first range of ($R_{mmin}$, $R_{mmax}$), assuming that the average amplitude value of the left-eye EMG information falls in a second range of ($L_{mmin}$, $L_{mmax}$), and assuming that the right eye is the dominant eye, then $L_{mmax}<R_{mmin}$, and the threshold may be determined as $M_m$, and $L_{mmax}<M_m<R_{mmin}$. That is, the threshold $M_m$ is a numerical value between the first range and the second range.

Therefore, if the average amplitude value of the first EMG information is greater than the threshold $M_m$, the average amplitude value of the first EMG information is considered as falling in the first range, and the first eye is the dominant eye of the user; and if the average amplitude value of the first EMG information is less than the threshold $M_m$, the average amplitude value of the first EMG information is considered as falling in the second range, and the first eye is not the dominant eye of the user.

d) The first sensory information may also be the EEG information corresponding to the first eye, that is, first EEG information. The determining module 1820 is configured to determine whether the first eye is the dominant eye according to the first EEG information and the reference information.

Figure 25:
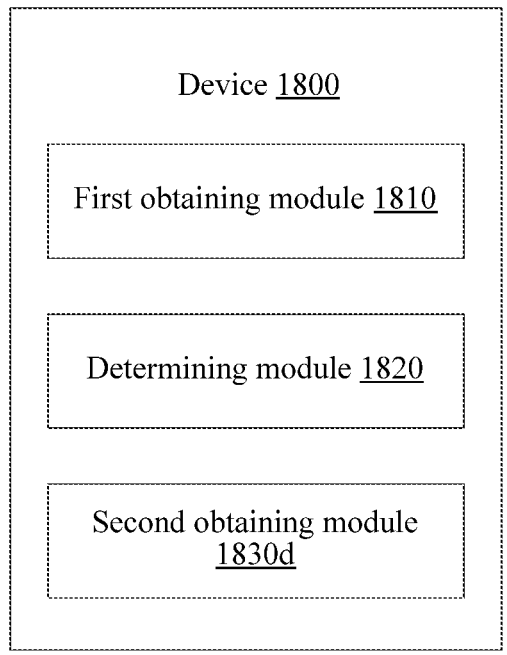
FIG. 25 is a schematic structural module diagram of a dominant eye determining device in another example embodiment of this application.

In an example embodiment, the reference information may be second EEG information corresponding to a second eye of the user. Referring to FIG. 25, the device 1800 may further comprise:

a second obtaining module 1830d, configured to obtain second EEG information corresponding to a second eye of the user as the reference information.

Correspondingly, the determining module 1820 is configured to: in response to that an average amplitude value of the first EEG information is greater than an average amplitude value of the second EEG information, determine that the first eye is the dominant eye; and in response to that an average amplitude value of the first EEG information is less than an average amplitude value of the second EEG information, determine that the first eye is not the dominant eye.

Figure 26:
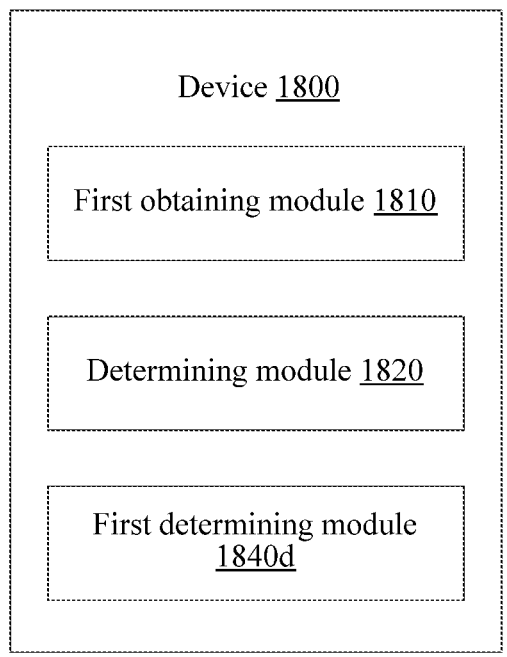
FIG. 26 is a schematic structural module diagram of a dominant eye determining device in another example embodiment of this application.

In another example embodiment, the reference information is a threshold determined according to an average amplitude value of left-eye EEG information of the user and an average amplitude value of right-eye EEG information of the user. Referring to FIG. 26, the device 1800 may comprise:

a first determining module 1840d, configured to determine a threshold as the reference information according to an average amplitude value of left-eye EEG information of the user and an average amplitude value of right-eye EEG information of the user.

Correspondingly, the determining module 1820 is configured to: in response to that an average amplitude value of the first EEG information is greater than the threshold, determine that the first eye is the dominant eye; and in response to that an average amplitude value of the first EEG information is less than the threshold, determine that the first eye is not the dominant eye.

For example, the first determining module 1840d may collect in advance the left-eye EEG information and the right-eye EEG information of the user, and perform analyzing and processing. Assuming that the average amplitude value of the right-eye EEG information falls in a first range of ($R_{emin}$, $R_{emax}$), assuming that the average amplitude value of the left-eye EEG information falls in a second range of ($L_{emin}$, $L_{emax}$), and assuming that the right eye is the dominant eye, then $L_{emax}<R_{emin}$, and the threshold may be determined as $M_e$, and $L_{emax}<M_e<R_{emin}$. That is, the threshold $M_e$ is a numerical value between the first range and the second range.

Therefore, if the average amplitude value of the first EEG information is greater than the threshold $M_e$, the average amplitude value of the first EEG information is considered as falling in the first range, and the first eye is the dominant eye; and if the average amplitude value of the first EEG information is less than the threshold $M_e$, the average amplitude value of the first EEG information is considered as falling in the second range, and the first eye is not the dominant eye.

Figure 27:
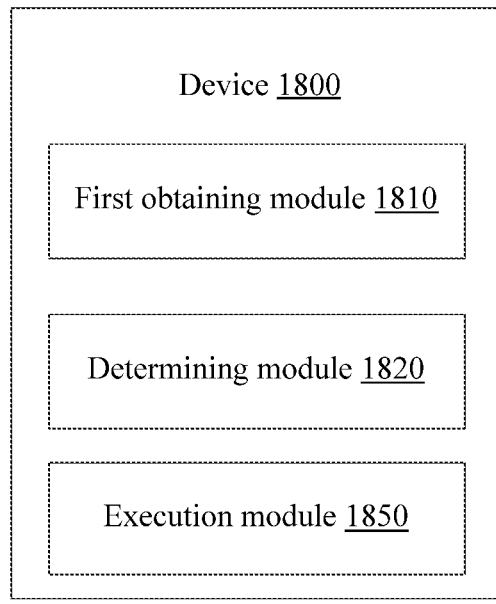
FIG. 27 is a schematic structural module diagram of a dominant eye determining device in another example embodiment of this application.

Referring to FIG. 27, in an example embodiment, the device 1800 may further comprise:

an execution module 1850, configured to perform operation according to a determining result.

For example, that the first eye is the dominant eye is displayed according to the determining result. If the user is playing a shooting game, the execution module 1850 may prompt the user to use the first eye to perform aiming, so as to improve immersive interaction experience of the user; or, if the user is viewing a 3D film, the execution module 1850 may perform automatic stereo 3D display at different viewing angles on the dominant eye and non-dominant eye of the user, to improve visual experience of the user.

Figure 28:
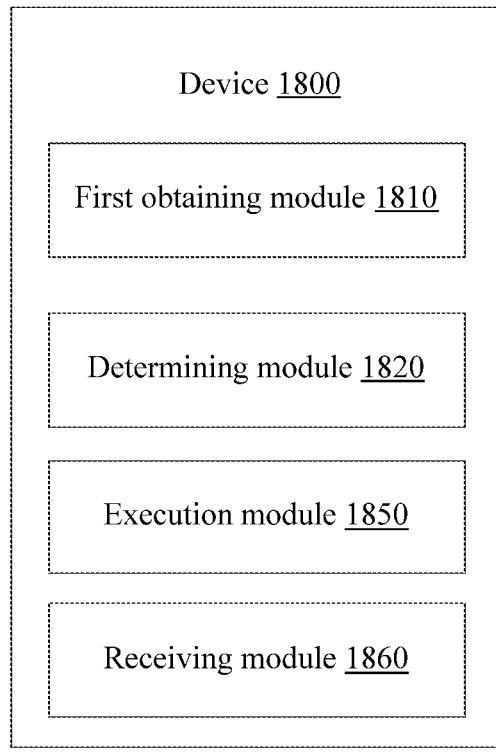
FIG. 28 is a schematic structural module diagram of a dominant eye determining device in another example embodiment of this application.

Referring to FIG. 28, in an example embodiment, the device 1800 may further comprise:

a receiving module 1860, configured to receive input information of the user.

The user may perform input in a manner of such as voice, key pressing, or gesture.

Figure 29:
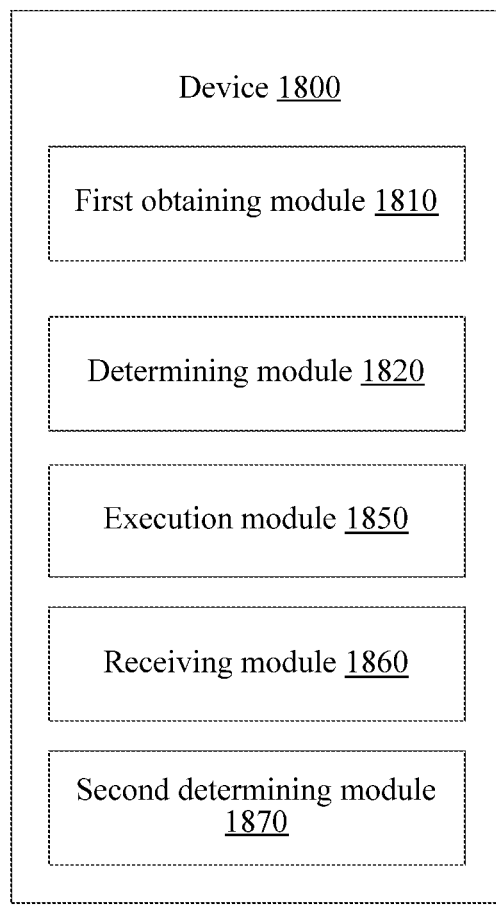
FIG. 29 is a schematic structural module diagram of a dominant eye determining device in another example embodiment of this application.

Referring to FIG. 29, in an example embodiment, the input information is dominant eye information, the device 1800 may further comprise:

a second determining module 1870, configured to determine that the first eye is the left eye or the right eye according to the input information and a determining result.

For example, the input information shows that the right eye of the user is the dominant eye, and the determining result shows that the first eye is the dominant eye, and then it may be determined that the first eye is the right eye.

After it is determined that the first eye is the left eye or the right eye, related settings of the left eye and right eye may be performed further, for example, a glass lens degree corresponding to the right eye is automatically adjusted to match with a myopic degree of the right eye of the user.

Figure 30:
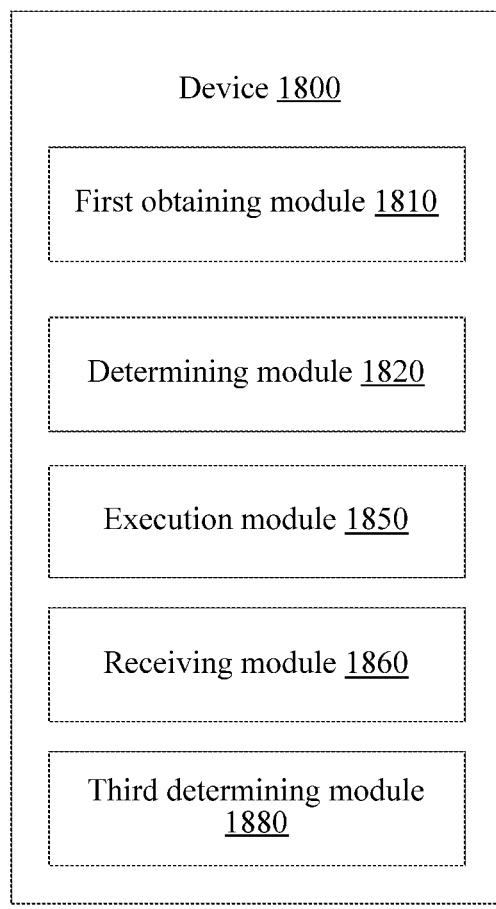
FIG. 30 is a schematic structural module diagram of a dominant eye determining device in another example embodiment of this application.

Referring to FIG. 30, in an example embodiment, the input information comprises that the first eye is the left eye or the right eye, the device 1800 may further comprise:

a third determining module 1880, configured to determine whether the left eye or the right eye of the user is the dominant eye according to the input information and a determining result.

For example, the input information shows that the first eye is the left eye, and the determining result shows that the first eye is the dominant eye, then it may be determined that the left eye of the user is the dominant eye, and this information may be recorded to be called by another application.

An application scenario of the dominant eye determining method and device in the embodiments of this application may be as follows: A user wears a smart helmet to play a shooting game. The smart helmet separately collects EEG signals corresponding to two eyes of the user at FP1 and FP2 areas of the brain of the user 1 minute before starting of the game, and it is determined that the left eye of the user is the dominant eye according to an analysis result; then, the user is prompted to use the left eye to perform aiming during the process of the game, the user uses the left eye to perform aiming according to the prompt, and accuracy of shooting is significantly improved, thereby improving user experience.

Figure 31:
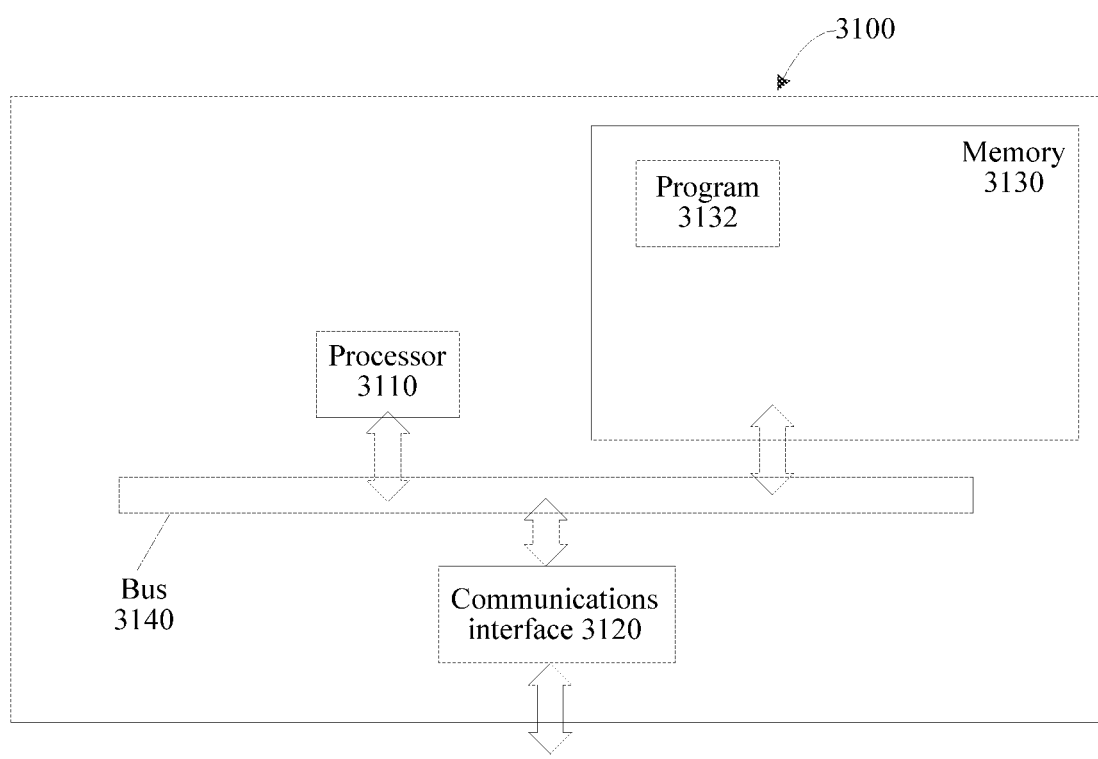
FIG. 31 is a schematic structural hardware diagram of a dominant body determining apparatus in an embodiment of this application.

FIG. 31 is a schematic structural hardware diagram of a dominant eye determining device in an embodiment of this application. A specific embodiment of this application is not intended to limit specific implementation of the dominant eye determining device. Referring to FIG. 31, the device 3100 may comprise:

a processor 3110, a communications interface 3120, a memory 3130 and a communications bus 3140.

Communication between the processor 3110, the communications interface 3120 and the memory 3130 is implemented by using the communications bus 3140.

The communications interface 3120 is configured to communicate with other network elements.

The processor 3110 is configured to execute a program 3132, and may specifically perform related steps in the method embodiment show in FIG. 1.

Specifically, the program 3132 may comprise program code, and the program code comprises computer operating instructions.

The processor 3110 may be a central processing unit (CPU), or an application specific integrated circuit (ASIC), or one or more integrated circuits configured to implement the embodiments of this application.

The memory 3130 is configured to store the program 3132. The memory 3130 may comprise a high-speed RAM, or may also comprise a non-volatile memory, for example, at least one magnetic disk storage. The program 3132 may specifically execute the following steps:

obtaining first sensory information of a first eye of a user; and determining whether the first eye is a dominant eye according to the first sensory information and reference information.

For specific implementation of the steps in the program 3132, reference may be made to corresponding steps or modules in the foregoing embodiments, and no further details are provided herein again. It may be clearly understood by a person skilled in the art that for convenience and simplicity of description, for specific working procedures of the devices and modules described above, reference may be made to corresponding descriptions of processes in the foregoing method embodiment, and no further details are provided herein again.

A person of ordinary skill in the art may be aware that, in combination with the examples described in the embodiments disclosed in this specification, units and method steps may be implemented by electronic hardware, or a combination of computer software and electronic hardware. Whether the functions are performed by hardware or software depends on the particular applications and design constraint conditions of the technical solution. A person skilled in the art may use different methods to implement the described functions for each particular application, but it should not be considered that the implementation goes beyond the scope of this application.

When the functions are implemented in a form of a software functional module and sold or used as an independent product, the functions may be stored in a computer-readable storage medium. Based on such an understanding, the technical solutions of this application essentially, or the part contributing to the prior art, or a part of the technical solutions may be implemented in a form of a software product. The computer software product is stored in a storage medium and comprises several instructions for instructing a computer device (which may be a personal computer, a controller, a network device, or the like) to perform all or a part of the steps of the methods described in the embodiments of this application. The foregoing storage medium comprises: any medium that can store program code, such as a USB flash drive, a removable hard disk, a read-only memory (ROM), a random access memory (RAM), a magnetic disk, or an optical disc.

The foregoing example embodiments are merely used to describe this application, but are not intended to limit this application. A person of ordinary skill in a related art may still make various variations and replacements within the spirit and scope of this application, therefore all equivalent technical solutions shall fall within the scope of this application, and the patent protection scope of this application shall be subject to the appended claims.

What is claimed is:

1. A method, comprising:
obtaining, by a device comprising a processor, first sensory information of a first eye of a user, wherein the first sensory information is one of: first electro-oculogram (EOG) information, first electromyogram (EMG) information, first electroencephalogram (EEG) information, or first temperature information; and
determining whether the first eye is a dominant eye according to the first sensory information and reference information.

2. The method of claim 1, wherein the reference information is a threshold determined according to a first average amplitude value of left-eye EOG information of the user and a second average amplitude value of right-eye EOG information of the user.

3. The method of claim 2, wherein the determining whether the first eye is the dominant eye according to the first EOG information and the reference information comprises:
in response to determining that a third average amplitude value of the first EOG information is greater than the threshold, determining that the first eye is the dominant eye; and
in response to determining that the third average amplitude value of the first EOG information is less than the threshold, determining that the first eye is not the dominant eye.

4. The method of claim 1, wherein the method further comprises:
obtaining second EOG information of a second eye of the user as the reference information.

5. The method of claim 4, wherein the determining whether the first eye is the dominant eye according to the first EOG information and the reference information comprises:
in response to determining that a first average amplitude value of the first EOG information is greater than a second average amplitude value of the second EOG information, determining that the first eye is the dominant eye; and
in response to determining that the first average amplitude value of the first EOG information is less than the second average amplitude value of the second EOG information, determining that the first eye is not the dominant eye.

6. The method of claim 1, wherein the reference information is a threshold determined according to a first average amplitude value of left-eye EMG information of the user and a second average amplitude value of right-eye EMG information of the user.

7. The method of claim 6, wherein the determining whether the first eye is the dominant eye according to the first EMG information and the reference information comprises:
in response to determining that a third average amplitude value of the first EMG information is greater than the threshold, determining that the first eye is the dominant eye; and
in response to determining that the third average amplitude value of the first EMG information is less than the threshold, determining that the first eye is not the dominant eye.

8. The method of claim 1, further comprising:
obtaining second EMG information of a second eye of the user as the reference information.

9. The method of claim 8, wherein the determining whether the first eye is the dominant eye according to the first EMG information and the reference information comprises:
in response to determining that a first average amplitude value of the first EMG information is greater than a second average amplitude value of the second EMG information, determining that the first eye is the dominant eye; and
in response to determining that the first average amplitude value of the first EMG information is less than the second average amplitude value of the second EMG information, determining that the first eye is not the dominant eye.

10. The method of claim 1, wherein the reference information is a threshold determined according to a first average amplitude value of left-eye EEG information of the user and a second average amplitude value of right-eye EEG information of the user.

11. The method of claim 10, wherein the determining whether the first eye is the dominant eye according to the first EEG information and the reference information comprises:
in response to determining that a third average amplitude value of the first EEG information is greater than the threshold, determining that the first eye is the dominant eye; and
in response to determining that the third average amplitude value of the first EEG information is less than the threshold, determining that the first eye is not the dominant eye.

12. The method of claim 1, further comprising:
obtaining second EEG information corresponding to a second eye of the user as the reference information.

13. The method of claim 12, wherein the determining whether the first eye is the dominant eye according to the first EEG information and the reference information comprises:
in response to determining that a first average amplitude value of the first EEG information is greater than a second average amplitude value of the second EEG information, determining that the first eye is the dominant eye; and
in response to determining that the first average amplitude value of the first EEG information is less than the second average amplitude value of the second EEG information, determining that the first eye is not the dominant eye.

14. The method of claim 1, wherein the reference information is a threshold determined according to a first average value of left-eye temperature information of the user and a second average value of right-eye temperature information of the user.

15. The method of claim 14, wherein the determining whether the first eye is the dominant eye according to the first temperature information and the reference information comprises:
in response to determining that a third average value of the first temperature information is greater than the threshold, determining that the first eye is the dominant eye; and
in response to determining that the third average value of the first temperature information is less than the threshold, determining that the first eye is not the dominant eye.

16. The method of claim 1, further comprising:
obtaining second temperature information of a second eye of the user as the reference information.

17. The method of claim 16, wherein the determining whether the first eye is the dominant eye according to the first temperature information and the reference information comprises:
in response to determining that a first average value of the first temperature information is greater than a second average value of the second temperature information, determining that the first eye is the dominant eye; and
in response to determining that the first average value of the first temperature information is less than the second average value of the second temperature information, determining that the first eye is not the dominant eye.

18. The method of claim 1, further comprising: performing operation according to a determining result.

19. The method of claim 1, further comprising: receiving input information of the user.

20. The method of claim 19, wherein the input information is dominant eye information, and the method further comprises:
determining that the first eye is a left eye or a right eye according to the input information and a determining result.

21. The method of claim 19, wherein the input information indicates that the first eye is a left eye of the user or a right eye of the user, and the method further comprises:
determining whether the left eye or the right eye of the user is the dominant eye according to the input information and a determining result.

22. A device, comprising:
at least one sensor;
a memory that stores executable modules; and
a processor, coupled to the memory, that executes or facilitates execution of the executable modules, the executable modules comprising:
a first obtaining module configured to obtain, with the at least one sensor, first sensory information of a first eye of a user, wherein the first sensory information is one of: first electro-oculogram (EOG) information, first electromyogram (EMG) information, first electroencephalogram (EEG) information, or first temperature information; and
a determining module configured to determine whether the first eye is a dominant eye according to the first sensory information and reference information.

23. The device of claim 22, wherein the executable modules further comprise:

a first determining module configured to determine a threshold as the reference information according to a first average amplitude value of left-eye EOG information of the user and a second average amplitude value of right-eye EOG information of the user.

24. The device of claim 23, wherein the determining module is configured to:
  in response to that a third average amplitude value of the first EOG information is greater than the threshold, determine that the first eye is the dominant eye; and
  in response to a determination that the third average amplitude value of the first EOG information is less than the threshold, determine that the first eye is not the dominant eye.

25. The device of claim 22, wherein the executable modules further comprise:
  a second obtaining module configured to obtain second EOG information of a second eye of the user as the reference information.

26. The device of claim 25, wherein the determining module is configured to:
  in response to a determination that a first average amplitude value of the first EOG information is greater than a second average amplitude value of the second EOG information, determine that the first eye is the dominant eye; and
  in response to a determination that the first average amplitude value of the first EOG information is less than the second average amplitude value of the second EOG information, determine that the first eye is not the dominant eye.

27. The device of claim 22, wherein the executable modules further comprise:
  a first determining module configured to determine a threshold as the reference information according to a first average amplitude value of left-eye EMG information of the user and a second average amplitude value of right-eye EMG information of the user.

28. The device of claim 27, wherein the determining module is configured to:
  in response to a determination that a third average amplitude value of the first EMG information is greater than the threshold, determine that the first eye is the dominant eye; and
  in response to a determination that the third average amplitude value of the first EMG information is less than the threshold, determine that the first eye is not the dominant eye.

29. The device of claim 22, wherein the executable modules further comprise:
  a second obtaining module configured to obtain second EMG information of a second eye of the user as the reference information.

30. The device of claim 29, wherein the determining module is configured to:
  in response to a determination that the first average amplitude value of the first EMG information is greater than the second average amplitude value of the second EMG information, determine that the first eye is the dominant eye; and
  in response to a determination that the first average amplitude value of the first EMG information is less than the second average amplitude value of the second EMG information, determine that the first eye is not the dominant eye.

31. The device of claim 22, wherein the executable modules further comprise:
  a first determining module configured to determine a threshold as the reference information according to a first average amplitude value of left-eye EEG information of the user and a second average amplitude value of right-eye EEG information of the user.

32. The device of claim 31, wherein the determining module is configured to:
  in response to a determination that a third average amplitude value of the first EEG information is greater than the threshold, determine that the first eye is the dominant eye; and
  in response to a determination that the third average amplitude value of the first EEG information is less than the threshold, determine that the first eye is not the dominant eye.

33. The device of claim 22, wherein the executable modules further comprise:
  a second obtaining module configured to obtain second EEG information corresponding to a second eye of the user as the reference information.

34. The device of claim 33, wherein the determining module is configured to:
  in response to a determination that a first average amplitude value of the first EEG information is greater than a second average amplitude value of the second EEG information, determine that the first eye is the dominant eye; and
  in response to a determination that the first average amplitude value of the first EEG information is less than the second average amplitude value of the second EEG information, determine that the first eye is not the dominant eye.

35. The device of claim 22, wherein the executable modules further comprise:
  a first determining module configured to determine a threshold as the reference information according to a first average value of left-eye temperature information of the user and a second average value of right-eye temperature information of the user.

36. The device of claim 35, wherein the determining module is configured to:
  in response to a determination that a third average value of the first temperature information is greater than the threshold, determine that the first eye is the dominant eye; and
  in response to a determination that the third average value of the first temperature information is less than the threshold, determine that the first eye is not the dominant eye.

37. The device of claim 22, wherein the executable modules further comprise:
  a second obtaining module configured to obtain second temperature information of a second eye of the user as the reference information.

38. The device of claim 37, wherein the determining module is configured to:
  in response to a determination that a first average value of the first temperature information is greater than a second average value of the second temperature information, determine that the first eye is the dominant eye; and
  in response to a determination that the first average value of the first temperature information is less than the second average value of the second temperature information, determine that the first eye is not the dominant eye.

39. The device of claim 22, wherein the executable modules further comprise:
an execution module configured to perform operation according to a determining result.

40. The device of claim 22, wherein the executable modules further comprise:
a receiving module configured to receive input information of the user.

41. The device of claim 40, wherein the input information is dominant eye information, and the executable modules further comprise:
a second determining module configured to determine that the first eye is a left eye or a right eye according to the input information and a determining result.

42. The device of claim 40, wherein the input information comprises that the first eye is the left eye or the right eye, and the executable modules further comprise:
a third determining module configured to determine whether the left eye or the right eye of the user is the dominant eye according to the input information and a determining result.

43. A wearable device, wherein the wearable device comprises the device of claim 22.

44. A non-transitory computer readable storage apparatus, comprising at least one executable instruction, which, in response to execution, causes a device comprising a processor to perform operations, comprising:
obtaining first sensory information of an eye of a user identity determined to be associated with the device, wherein the first sensory information is one of: first electro-oculogram (EOG) information, first electromyogram (EMG) information, first electroencephalogram (EEG) information, or first temperature information; and
determining whether the eye is a dominant eye according to the first sensory information and reference information.

45. The non-transitory computer readable storage apparatus of claim 44, wherein the reference information is a threshold determined according to a first average amplitude value of left-eye EOG information of the user and a second average amplitude value of right-eye EOG information of the user.

46. The non-transitory computer readable storage apparatus of claim 45, wherein the determining whether the first eye is the dominant eye according to the first EOG information and the reference information comprises:
in response to determining that a third average amplitude value of the first EOG information is greater than the threshold, determining that the first eye is the dominant eye; and
in response to determining that the third average amplitude value of the first EOG information is less than the threshold, determining that the first eye is not the dominant eye.

47. The non-transitory computer readable storage apparatus of claim 44, wherein the operations further comprise:
obtaining second EOG information of a second eye of the user as the reference information.

48. The non-transitory computer readable storage apparatus of claim 44, wherein the determining whether the first eye is the dominant eye according to the first EOG information and the reference information comprises:
in response to determining that a first average amplitude value of the first EOG information is greater than a second average amplitude value of the second EOG information, determining that the first eye is the dominant eye; and
in response to determining that the first average amplitude value of the first EOG information is less than the second average amplitude value of the second EOG information, determining that the first eye is not the dominant eye.

49. The non-transitory computer readable storage apparatus of claim 44, wherein the reference information is a threshold determined according to a first average amplitude value of left-eye EMG information of the user and a second average amplitude value of right-eye EMG information of the user.

50. The non-transitory computer readable storage apparatus of claim 49, wherein the determining whether the first eye is the dominant eye according to the first EMG information and the reference information comprises:
in response to determining that a third average amplitude value of the first EMG information is greater than the threshold, determining that the first eye is the dominant eye; and
in response to determining that the third average amplitude value of the first EMG information is less than the threshold, determining that the first eye is not the dominant eye.

51. The non-transitory computer readable storage apparatus of claim 44, wherein the operations further comprise:
obtaining second EMG information of a second eye of the user as the reference information.

52. The non-transitory computer readable storage apparatus of claim 51, wherein the determining whether the first eye is the dominant eye according to the first EMG information and the reference information comprises:
in response to determining that a first average amplitude value of the first EMG information is greater than a second average amplitude value of the second EMG information, determining that the first eye is the dominant eye; and
in response to determining that the first average amplitude value of the first EMG information is less than the second average amplitude value of the second EMG information, determining that the first eye is not the dominant eye.

53. A dominant eye determining device, characterized by comprising a processor and a memory, the memory storing executable instructions, the processor being connected to the memory through a communication bus, and when the dominant eye determining device operates, the processor executes or facilitates execution of the executable instructions stored in the memory, so that the dominant eye determining device executes operations, comprising:
obtaining first sensory information of a first eye of a user identity determined to be associated with the dominant eye determining device, wherein the first sensory information is one of: first electro-oculogram (EOG) information, first electromyogram (EMG) information, first electroencephalogram (EEG) information, or first temperature information; and
determining whether the first eye is a dominant eye according to the first sensory information and reference information.

* * * * *